(12) United States Patent
Xu et al.

(10) Patent No.: US 11,324,941 B2
(45) Date of Patent: May 10, 2022

(54) INTRAVENTRICULAR PULSATING BLOOD PUMP

(71) Applicant: SOOCHOW UNIVERSITY, Suzhou (CN)

(72) Inventors: Boling Xu, Suzhou (CN); Weiguo Dang, Suzhou (CN); Penghui Huang, Suzhou (CN)

(73) Assignee: magAssist Inc., Suzhou (CN)

( * ) Notice: Subject to any disclaimer, the term of this patent is extended or adjusted under 35 U.S.C. 154(b) by 361 days.

(21) Appl. No.: 16/484,833

(22) PCT Filed: Oct. 21, 2016

(86) PCT No.: PCT/CN2016/102856
§ 371 (c)(1),
(2) Date: Aug. 9, 2019

(87) PCT Pub. No.: WO2018/068341
PCT Pub. Date: Apr. 19, 2018

(65) Prior Publication Data
US 2020/0038570 A1 Feb. 6, 2020

(30) Foreign Application Priority Data

Oct. 13, 2016 (CN) .......................... 201610891191.4

(51) Int. Cl.
*A61M 60/40* (2021.01)
*A61M 60/148* (2021.01)
*A61M 60/268* (2021.01)

(52) U.S. Cl.
CPC ........ *A61M 60/148* (2021.01); *A61M 60/268* (2021.01); *A61M 60/40* (2021.01); *A61M 2206/10* (2013.01); *A61M 2210/125* (2013.01)

(58) Field of Classification Search
CPC ........ A61M 2206/10; A61M 2210/125; A61M 60/148; A61M 60/268; A61M 60/40
See application file for complete search history.

(56) References Cited

U.S. PATENT DOCUMENTS

| 4,771,765 A | 9/1988 | Choy et al. |
| 6,387,042 B1 | 5/2002 | Herrero |

(Continued)

FOREIGN PATENT DOCUMENTS

| CN | 201040049 A | 3/2008 |
| CN | 101336119 A | 12/2008 |

(Continued)

*Primary Examiner* — George Manuel
(74) *Attorney, Agent, or Firm* — SZDC Law P.C.

(57) ABSTRACT

The invention provides an intraventricular pulsating blood pump fixedly disposed at the ventricularapex inside the ventricle to generate pulsation action. The pulsating blood pump is substantially jellyfish-shaped and includes a bell-shaped pump body and a driving source, an opening of the bell-shaped pump body faces to the outlet of the ventricle, the driving source drives the bell-shaped pump body to contract or relax, and the contraction or relaxation of the bell-shaped pump body drives the blood in the ventricle to eject directionally to the artery and form a convoluted blood flow field between the inner wall of the bell-shaped pump body and the inner wall of the ventricle. The invention not only provides assist to ventricular by pulsating blood flow, but also optimizes the flow field and pressure distribution in the ventricle, the blood pump of the invention is better in biocompatibility than the blood pumps in prior art.

7 Claims, 2 Drawing Sheets

(56) References Cited

U.S. PATENT DOCUMENTS

| | | |
|---|---|---|
| 2004/0249408 A1 | 12/2004 | Murphy et al. |
| 2005/0228211 A1 | 10/2005 | Leasure |
| 2006/0142634 A1* | 6/2006 | Anstadt ............... A61M 60/268 600/16 |
| 2009/0177028 A1 | 7/2009 | White |
| 2014/0179993 A1 | 6/2014 | Alexander et al. |
| 2015/0182679 A1 | 7/2015 | Parker et al. |

FOREIGN PATENT DOCUMENTS

| | | | |
|---|---|---|---|
| CN | 102405590 | A | 4/2012 |
| CN | 102460756 | A | 5/2012 |
| CN | 102872486 | A | 1/2013 |
| CN | 104220037 | A | 12/2014 |
| WO | 2006111954 | A2 | 10/2006 |
| WO | 2007066344 | A1 | 6/2007 |

* cited by examiner

INTRAVENTRICULAR PULSATING BLOOD PUMP

This application is the National Stage Application PCT/CN2016/102856, filed on Oct. 21, 2016, which claims priority to Chinese Patent Application No.: 201610891191.4, filed on Oct. 13, 2016, which is incorporated by reference for all purposes as if fully set forth herein.

TECHNICAL FIELD

The invention relates to the field of ventricular assist devices, and more particularly to an intraventricular pulsating blood pump.

BACKGROUND

The ventricular assist device (blood pump) is a mechanical circulation assist device made of artificial materials to assist heart pumping of patients with end-stage heart failure. This type of device has been clinically applied in occident and successfully saved or continued the lives of a large number of patients with heart disease.

At present, most of the blood pumps in the world that have been put into clinical application or are in the research and development stage are based on the basic principle of rotary turbomachinery, with the rotational action between the blade and the blood, to achieve blood pumping in the centrifugal or axial flow manners by the rotation of the blade. The principle thereof is to connect the inlet section of the blood pump to the ventricle, the outlet section to the artery, and the blood flow formed by the rotation of the blade is used to assist to enhance the cardiac output of the ventricle. The blood pump is usually implanted at a position outside the ventricle such as the outer wall of the ventricle or the ventricularapex. The blood flow provided by a rotary mechanical blood pump is usually continuous, i.e. the flow rate does not change over time. But some blood pumps also have the function of providing pulsating blood flow, i.e. the flow rate changes over time similar to the pulsation effect of the human heart.

U.S. application 2015/0182679 A1, entitled "TISSUE-ENGINEERED PUMPS AND VALVES AND USES THEREOF", discloses a biomimetic jellyfish made of biological tissue material as a design for an artificial heart.

Traditional centrifugal or axial flow blood pumps that use blades as actuators have several major drawbacks:

1. the inlet of the ventricular assist device in prior art forms an uneven pressure distribution in the ventricle, which easily causes negative effects in the ventricle, including suction and thrombus;

2. the ventricular assist device in prior art changes the original blood flow mode, resulting in closure of the artery flap for a long time, which has a negative impact on the valve (valvular incompetence, sclerosis, sticky, etc.);

3. the ventricular assist device in prior art is a rotary continuous blood flow pump whose action produces continuous shear force to the blood, leading to hemolysis and blood-related complications. The blade made of rigid material (such as metal) produces large and continuous shear stress to the blood during the high speed rotary motion, resulting in damage to blood cells, and thus resulting in hemolysis and thrombus, and resulting in postoperative sequelae to the patients implanted with blood pumps such as stroke;

4. since the blood pumping process takes place in a closed shell-like structure, the flow field dead zone usually occurs due to the mechanical structure design, causing the blood in some dead zones to be stagnant for a long time, which leads to coagulation.

The above-mentioned problem of flow field dead zone not only occurs in the blood pumps with blades, but also in the above-mentioned U.S. patent, which uses a flexible material as an actuator, since it adopts a closed-heart-assisted technology, it also causes a problem of flow field dead zone. Some other pulsating blood pump cannot avoid the problem of blood compatibility at the joint of the valve switch because of the use of the artificial valve mechanism. The clinical results show that the blood compatibility is even worse than that of the blood pumps with blades.

SUMMARY OF THE INVENTION

In order to solve the above technical problems, an object of the present invention is to provide an intraventricular pulsating blood pump, to solve the shortcomings of the conventional axial flow or centrifugal blood pump and other closed pulsating blood pumps with poor biocompatibility.

In order to achieve the above object, the present invention provides the following technical solution: an intraventricular pulsating blood pump, which generates an open pulsation action, and is fixedly disposed at the ventricularapex inside the ventricle. The intraventricular pulsating blood pump is generally jellyfish-shaped and includes a bell-shaped pump body and a driving source, an opening of the bell-shaped pump body faces to an outlet of the ventricle, and the driving source drives contraction and relaxation of the bell-shaped pump body to change the volume of an inner cavity of the bell-shaped pump body, when the volume of the inner cavity is reduced, the blood in the bell-shaped pump body is pressed outwards, thereby realizing blood ejection to the ventricle, and when the volume of the inner cavity is increased, the blood outside of the bell-shaped pump body is inhaled into the bell-shaped pump body to provide blood for the next blood ejection.

Preferably, the contraction and relaxation of the bell-shaped pump body allows the blood to produce the Venturi effect, thereby producing a convoluted blood flow field.

Preferably, when the bell-shaped pump body contracts, the volume of the inner cavity is reduced, so that a scouring blood flow field is created for the inner wall of the ventricle.

Preferably, when the bell-shaped pump body relaxes, the volume of the inner cavity is increased, so that a scouring blood flow field is created for the inner wall of the bell-shaped pump body.

Preferably, the bell-shaped pump body comprises a skeleton having a bell-shaped structure and a film coated on the skeleton.

Preferably, the skeleton is constituted by a mechanical link structure, and the driving source is a motor or a cylinder.

Preferably, the skeleton comprises an end cap portion at an end thereof, at least three rocker structures respectively located at different generatrix thereof, and a driving link structure at an inner side thereof. The end cap portion is fixedly disposed. The rocker structure include a first rocker and a second rocker, one end of the first rocker is hingedly connected with the end cap portion to constitute a first movable joint, one end of the second rocker is hingedly connected with the other end of the first rocker to constitute a second movable joint. The driving link structure includes a driving rod and at least three third rockers corresponding to the rocker structures, a rod body of the driving rod is axially coupled to the end cap portion and forms an inner end portion at the inner side of the skeleton and an outer end portion at the outer side of the skeleton, the inner end portion of the driving rod is hingedly connected with one end of the third rocker, and the other end of the third rocker is hingedly connected with a sliding block, and the sliding block is slidably connected on the second rocker, the outer end portion of the driving rod is connected to the driving source.

Preferably, an angle range of the first rocker relative to the driving rod is 0-50 degrees, and an angle range of the second rocker relative to the driving rod is 30-50 degrees.

Preferably, the stroke of the driving rod is 5-7 mm.

Preferably, the skeleton is made of a dielectric elastomer material, and the driving source is an electric field.

Due to the above technical solutions, the open pulsation of the present invention not only provides assist to ventricular by pulsating blood flow, but also optimizes the flow field and pressure distribution in the ventricle, which is better in biocompatibility than the blood pumps in prior art, which is described in detail as follows:

1. all blood enters the cardiovascular system through the original passage (atrioventricular valve-ventricle-aortic valve-arteries), and a good intraventricular pressure distribution is formed to create a scouring blood flow field, avoiding thrombus caused by flow field dead zone;

2. a local negative pressure is not formed in the ventricle, and directional blood ejection is provided during work;

3. the actuator made of a flexible material can greatly reduce the continuous non-physiological shear stress to the blood when the blood pump is working, reducing the possibility of hemolysis and thrombosis.

Wherein, 1, ventricle; 2, pulsating blood pump; 3, skeleton of the bell-shaped pump body; 31, end cap portion; 32, first rocker; 33, second rocker; 34, driving rod; 35, third rocker; 36, sliding block; 4, elastic film; 5, bell-shaped pump body.

DETAILED DESCRIPTION OF THE EMBODIMENTS

The invention will be further illustrated in more detail with reference to the accompanying drawings and embodiments. It is noted that, the following embodiments only are intended for purposes of illustration, but are not intended to limit the scope of the present invention.

Embodiment 1

Figure 1:
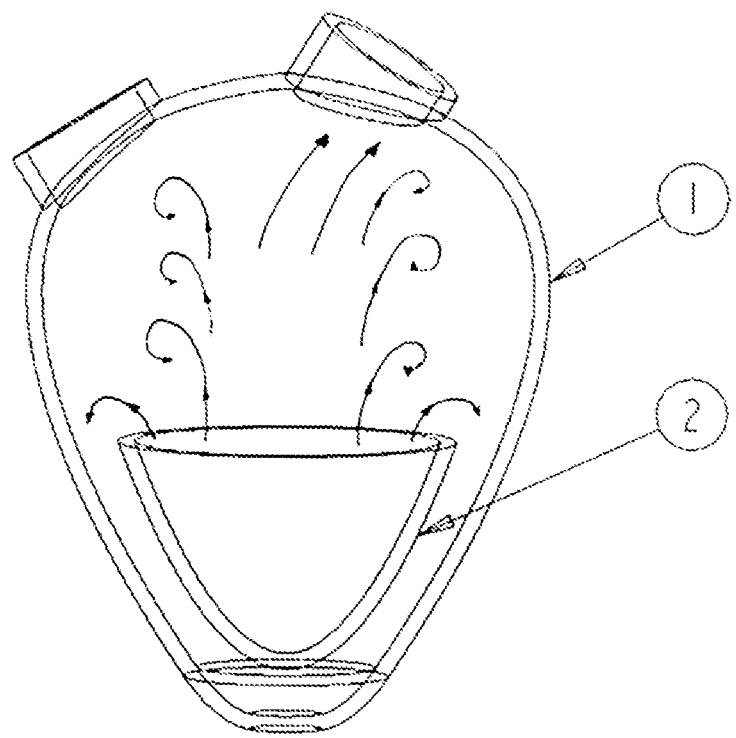
FIG. 1 is a schematic view of the intraventricular pulsating blood pump of the present invention, wherein the blood pump begins to contract in the ventricle.
Figure 2:
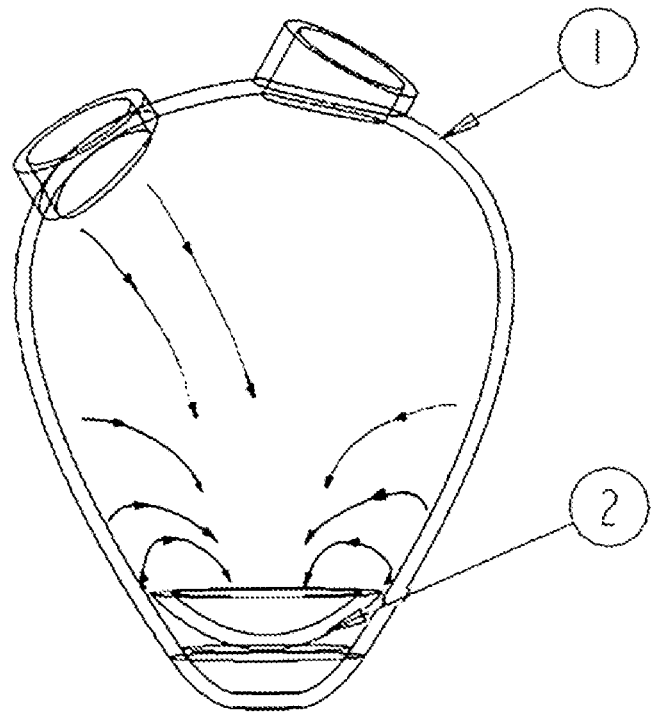
FIG. 2 is a schematic view of the intraventricular pulsating blood pump of the present invention, when the blood pump begins to relax in the ventricle.
Figure 3:
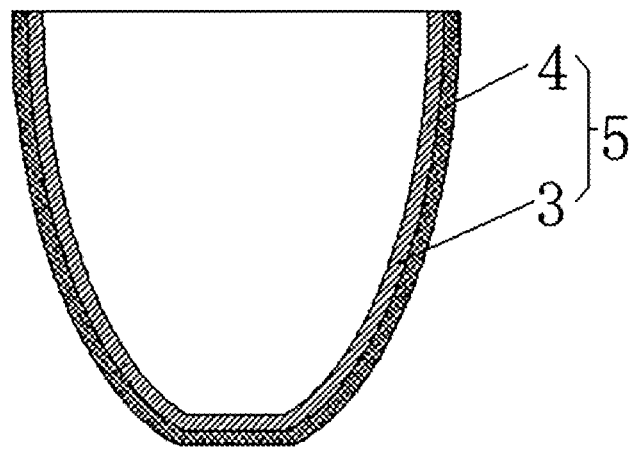
FIG. 3 is a schematic view of a bell-shaped pump body of the present invention.
Figure 4:
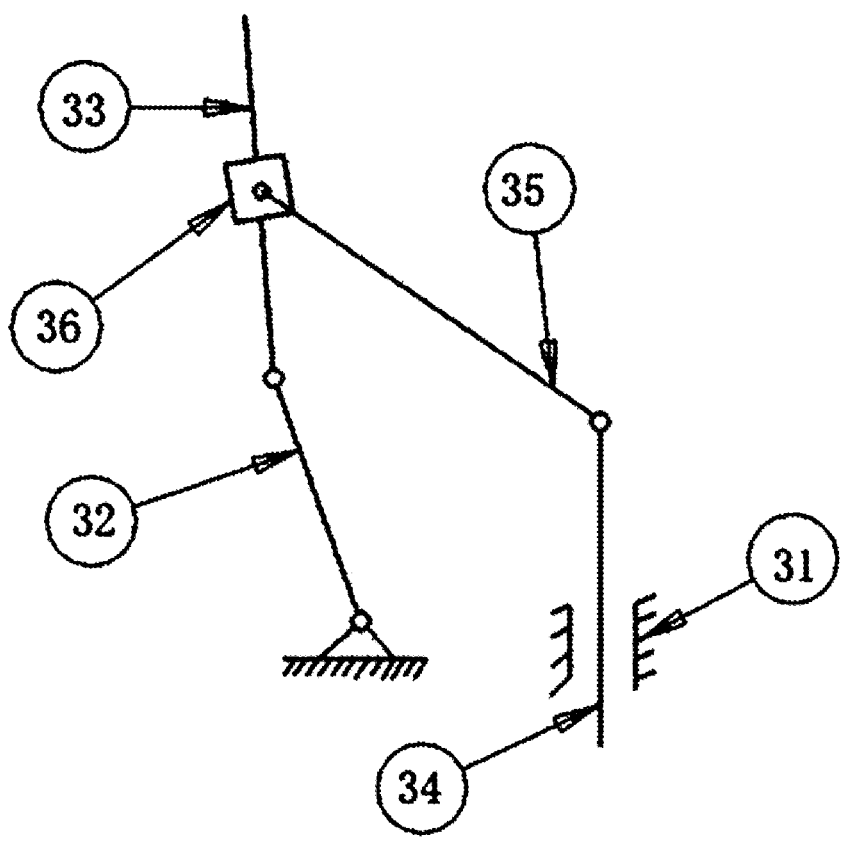
FIG. 4 is a schematic view showing the connection of a mechanical link structure of a skeleton of the bell-shaped pump body according to the present invention.

Referring to FIG. 1 to FIG. 4, an intraventricular pulsating blood pump is shown, the pulsating blood pump 2 is fixedly disposed at the ventriculararpex inside the ventricle 1 and is generally jellyfish-shaped. The pulsating blood pump 2 includes a skeleton 3, an elastic film 4 and a driving source, the elastic film 4 covers on the outer side of the skeleton 3 to form a bell-shaped pump body 5, the outlet of the bell-shaped pump body 5 faces to the outlet of the ventricle 1. The driving source is coupled to the skeleton 3 to drive the bell-shaped pump body 5 to contract or relax, the contraction or relaxation of the bell-shaped pump body 5 drives the blood in the ventricle 1 to eject directionally to the artery, and forms a convoluted blood flow field between the inner wall of the bell-shaped pump body 5 and the inner wall of the ventricle 1.

Inspired by the principle of jellyfish swimming, the invention provides a non-rotatory bionic intraventricular pulsating blood pump. The body of jellyfish has a bell-shaped structure, the jellyfish shrinks the bell-shaped pump body to change the volume of the inner cavity when swimming, thus ejecting the water in the cavity. The propulsive force generated by this ejection process allows the jellyfish to move axially along its body. In accordance with the principle of jellyfish movement, the present invention utilizes a linkage mechanism to form a bionic jellyfish bell-shaped skeleton, and a flexible material is wrapped around the skeleton to form an entire bionic jellyfish structure, and then a linear motor drives the linkage mechanism to contract and relax, thereby achieving the ejecting function.

The contraction or relaxation of the bell-shaped pump body 5 produces the Venturi effect in the above-mentioned convoluted blood flow field, and when the bell-shaped pump body 5 contracts, a scouring flow field is generated on the inner wall of the ventricle 1, and when the bell-shaped pump body 5 relaxes, a scouring flow field is generated on the inner wall of the bell-shaped pump body 5.

The bell-shaped skeleton 3 is constituted by a mechanical link structure, and the driving source is a linear motor.

The bell-shaped skeleton 3 comprises an end cap portion 31 at an end thereof, at least three rocker structures respectively located at different generatrix thereof, and a driving link structure at an inner side thereof. The end cap portion 31 is fixedly disposed. The above rocker structure includes a first rocker 32 and a second rocker 33, one end of the first rocker 32 is hingedly connected with the end cap portion 31 to constitute a first movable joint, one end of the second rocker 33 is hingedly connected with the other end of the first rocker 32 to constitute a second movable joint. The above driving link structure includes a driving rod 34 and at least three third rockers 35 corresponding to the rocker structures, a rod body of the driving rod 34 is axially coupled to the end cap portion 31 and forms an inner end portion at the inner side of the skeleton 3 and an outer end portion at the outer side of the skeleton 3, the inner end portion of the driving rod 34 is hingedly connected with one end of the third rocker 35, and the other end of the third rocker 35 is hingedly connected with a sliding block 36, and the sliding block 36 is slidably connected on the second rocker 33, the outer end portion of the driving rod 34 is connected to the linear motor.

The driving rod 34 is connected to the linear motor to reciprocate vertically. One end of the third rocker 35 is hinged to the driving rod 34, and the other end is hinged with the sliding block 36. When the driving rod 34 starts to reciprocate under the driving of the linear motor, the sliding block 36 also reciprocates in the axial direction of the second rocker 33, which simultaneously drives the first rocker 32 and the second rocker 33 to oscillate, thereby achieving contraction and relaxation of the bell-shaped pump body 5.

An angle range of the first rocker 32 relative to the driving rod 34 is 0-50 degrees, and an angle range of the second rocker 33 relative to the driving rod 34 is 30-50 degrees.

The stroke of the driving rod 34 is 6 mm.

Embodiment 2

The intraventricular pulsating blood pump of Embodiment 2 is different from that of Embodiment 1 in that, the skeleton or the film is made of a dielectric elastomer material, the driving source is an electric field, and the dielectric elastomer material generates a large driving force and elastic deformation under the electric field to achieve contraction and relaxation.

Embodiment 3

The intraventricular pulsating blood pump of Embodiment 3 is different from that of Embodiment 1 in that, the driving source is an air cylinder.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. An intraventricular pulsating blood pump, which has an open pump body to generate pulsation action and is adapted to be fixedly disposed at the ventricularapex inside the ventricle, wherein the intraventricular pulsating blood pump is generally jellyfish-shaped and includes:
   a bell-shaped pump body, an opening of the bell-shaped pump body facing to an outlet of the ventricle; and
   a driving source, which drives contraction and relaxation of the bell-shaped pump body to change the volume of an inner cavity of the bell-shaped pump body, when the volume of the inner cavity is reduced, the blood in the bell-shaped pump body is pressed outwards, thereby realizing blood ejection to the ventricle, and when the volume of the inner cavity is increased, the blood outside of the bell-shaped pump body is inhaled into the bell-shaped pump body to provide blood for a next blood ejection,
   wherein the bell-shaped pump body comprises a skeleton having a bell-shaped structure and a film coated on the skeleton,
   wherein the skeleton is constituted by a mechanical link structure and the driving source is a motor or a cylinder,
   wherein the skeleton comprises:
   an end cap portion at an end thereof, which is fixedly disposed;
   at least three rocker structures respectively located at different generatrix thereof, the rocker structure including a first rocker and a second rocker, one end of the first rocker being hingedly connected with the end cap portion to constitute a first movable joint, one end of the second rocker being hingedly connected with the other end of the first rocker to constitute a second movable joint; and
   a driving link structure at an inner side thereof, the driving link structure including a driving rod and at least three third rockers corresponding to the rocker structures, wherein a rod body of the driving rod is axially coupled to the end cap portion and forms an inner end portion at the inner side of the skeleton and an outer end portion at the outer side of the skeleton, the inner end portion of the driving rod is hingedly connected with one end of the third rocker, and the other end of the third rocker is hingedly connected with a sliding block which is slidably connected on the second rocker, the outer end portion of the driving rod is connected to the driving source.

2. The intraventricular pulsating blood pump according to claim 1, wherein the contraction and relaxation of the bell-shaped pump body allows the blood to produce the Venturi effect, thereby producing a convoluted blood flow field.

3. The intraventricular pulsating blood pump according to claim 1, wherein when the bell-shaped pump body contracts, the volume of the inner cavity is reduced, so that a scouring blood flow field is created for the inner wall of the ventricle.

4. The intraventricular pulsating blood pump according to claim 1, wherein when the bell-shaped pump body relaxes, the volume of the inner cavity is increased, so that a scouring blood flow field is created for the inner wall of the bell-shaped pump body.

5. The intraventricular pulsating blood pump according to claim 1, wherein an angle range of the first rocker relative to the driving rod is 0-50 degrees and an angle range of the second rocker relative to the driving rod is 30-50 degrees.

6. The intraventricular pulsating blood pump according to claim 1, wherein a stroke of the driving rod is 5-7 mm.

7. The intraventricular pulsating blood pump according to claim 1, wherein the skeleton is made of a dielectric elastomer material and the driving source is an electric field.

* * * * *